(12) United States Patent
Nomura (10) Patent No.: US 6,758,819 B2
(45) Date of Patent: Jul. 6, 2004

(54) PULSE-WAVE-PROPAGATION-VELOCITY MEASURING APPARATUS

(75) Inventor: Takashi Nomura, Komaki (JP)

(73) Assignee: Colin Medical Technology Corporation, Komaki (JP)

(*) Notice: Subject to any disclaimer, the term of this patent is extended or adjusted under 35 U.S.C. 154(b) by 110 days.

(21) Appl. No.: 10/265,357

(22) Filed: Oct. 7, 2002

(65) Prior Publication Data

US 2003/0153839 A1 Aug. 14, 2003

(30) Foreign Application Priority Data

Feb. 8, 2002 (JP) ........................................ 2002-032025

(51) Int. Cl.[7] ................................................ A61B 5/02
(52) U.S. Cl. ..................... 600/481; 600/485; 600/500; 600/504
(58) Field of Search ................................ 600/481–507, 600/508

(56) References Cited

U.S. PATENT DOCUMENTS

| | | | |
|---|---|---|---|
| 5,197,019 A | * | 3/1993 | Delon-Martin et al. ..... 600/443 |
| 5,388,583 A | * | 2/1995 | Ragauskas et al. ......... 600/451 |
| 5,779,638 A | * | 7/1998 | Vesely et al. ............... 600/437 |
| 5,921,936 A | * | 7/1999 | Inukai et al. ............... 600/490 |
| 6,120,456 A | | 9/2000 | Oka et al. |
| 6,261,233 B1 | * | 7/2001 | Kantorovich ............... 600/454 |
| 6,315,734 B1 | * | 11/2001 | Nunome ..................... 600/500 |
| 6,331,162 B1 | | 12/2001 | Mitchell |
| 6,475,155 B2 | * | 11/2002 | Ogura et al. ................ 600/500 |
| 6,511,436 B1 | * | 1/2003 | Asmar ........................ 600/500 |

FOREIGN PATENT DOCUMENTS

| | | |
|---|---|---|
| EP | 0 498 281 A1 | 8/1992 |
| FR | 2 704 416 A1 | 11/1994 |

* cited by examiner

*Primary Examiner*—Mary Beth Jones
*Assistant Examiner*—Patricia C. Mallari
(74) *Attorney, Agent, or Firm*—Oliff & Berridge, PLC (57) ABSTRACT

An apparatus for measuring a velocity at which a pulse wave propagates between a first portion and a second portion of a living subject, the apparatus including a propagation-signal producing device which is adapted to be worn on the first portion of the subject and produces a propagation signal, a propagation-signal detecting device which is adapted to be worn on the second portion of the subject and detects the propagation signal that has been produced by the propagation-signal producing device, has propagated through a body tissue of the subject, and has reached the second portion, a blood-vessel-length determining device for determining a length of a blood vessel of the subject that is located between the first and second portions of the subject, based on a signal propagation time from a time when the propagation signal is produced by the propagation-signal producing device, to a time when the propagation signal is detected by the propagation-signal detecting device, and a pre-stored velocity at which the propagation signal propagates through a body tissue of a human person, and a pulse-wave-propagation-velocity determining device for determining the velocity at which the pulse wave propagates between the first and second portions of the subject, based on the length of the blood vessel determined by the blood-vessel-length determining device.

5 Claims, 6 Drawing Sheets

PULSE-WAVE-PROPAGATION-VELOCITY MEASURING APPARATUS

BACKGROUND OF THE INVENTION

1. Field of the Invention

The present invention relates to a pulse-wave-propagation-velocity measuring apparatus which measures a velocity at which a pulse wave propagates in a living subject.

2. Related Art Statement

Pulse-wave propagation velocity is utilized in various medical diagnoses. For example, since pulse-wave propagation velocity increases as artery hardens, the velocity is used in diagnosing arteriosclerosis. In addition, since pulse-wave propagation velocity changes in relation with changing of blood pressure, the velocity is used in monitoring the blood pressure.

A pulse-wave propagation velocity may be measured such that two heartbeat-synchronous signals (a pulse wave, a heart sound, an electrocardiograph signal, etc.) are detected from two portions of a living subject, a propagation time in which one of the two signals propagates between the two portions, is determined based on respective times when the two signals are detected, and the velocity is determined by dividing, by the propagation time, a length of an artery between the two portions.

In a conventional manner, a length of an artery is approximated by a value which is obtained by substituting a stature of a patient for an expression representing a relationship between stature and artery's length that is experimentally determined in advance, or a value which is measured, on a body surface, between the two portions.

Thus, in order to measure an accurate pulse-wave propagation velocity, it is needed to measure an accurate artery's length. However, the artery's length determined based on the patient's stature is not so accurate. In addition, the value measured on the body surface between the two portions is more accurate than the artery's length determined based on the patient's stature, but the accuracy of measurement depends on measurer's skill. In addition, the measuring operation needs a long time.

SUMMARY OF THE INVENTION

It is therefore an object of the present invention to provide a pulse-wave-propagation-velocity measuring apparatus which can accurately and quickly determine a length of an artery of a living subject.

The above object has been achieved by the present invention. According to a first aspect of the present invention, there is provided an apparatus for measuring a velocity at which a pulse wave propagates between a first portion and a second portion of a living subject, the apparatus comprising: a propagation-signal producing device which is adapted to be worn on the first portion of the subject and produces a propagation signal; a propagation-signal detecting device which is adapted to be worn on the second portion of the subject and detects the propagation signal that has been produced by the propagation-signal producing device, has propagated through a body tissue of the subject, and has reached the second portion; a blood-vessel-length determining means for determining a length of a blood vessel of the subject that is located between the first and second portions of the subject, based on a signal propagation time from a time when the propagation signal is produced by the propagation-signal producing device, to a time when the propagation signal is detected by the propagation-signal detecting device, and a pre-stored velocity at which the propagation signal propagates through a body tissue of a human person; and a pulse-wave-propagation-velocity determining means for determining the velocity at which the pulse wave propagates between the first and second portions of the subject, based on the length of the blood vessel determined by the blood-vessel-length determining means.

According to this aspect, the blood-vessel-length determining means determines, as a length of a blood vessel, a distance by which the propagation signal has propagated between the first and second portions of the subject where a pulse-wave propagation velocity is to be measured. Thus, the present apparatus can measure length of blood vessel with the same degree of accuracy as that with which length of blood vessel is measured on body surface between the two portions. In addition, since blood-vessel length can be determined by just wearing the propagation-signal producing device on the first portion and wearing the propagation-signal detecting device on the second portion, no skill is needed. Moreover, the time needed for the determination of blood-vessel length can be shortened.

Preferably, the measuring apparatus further comprises a first heartbeat-synchronous-signal detecting device which is adapted to be worn on the first portion of the subject and detects a first heartbeat-synchronous signal from the first portion; and a second heartbeat-synchronous-signal detecting device which is adapted to be worn on the second portion of the subject and detects a second heartbeat-synchronous signal from the second portion, and the pulse-wave-propagation-velocity determining means determines the velocity at which the pulse wave propagates between the first and second portions of the subject, by dividing the length of the blood vessel determined by the blood-vessel-length determining means, by a pulse-wave propagation time from a time when the first heartbeat-synchronous signal is detected by the first heartbeat-synchronous-signal detecting device, to a time when the second heartbeat-synchronous signal is detected by the second heartbeat-synchronous-signal detecting device. In addition, the propagation-signal producing device is supported by the first heartbeat-synchronous-signal detecting device, and the propagation-signal detecting device is supported by the second heartbeat-synchronous-signal detecting device.

Thus, when the first and second heartbeat-synchronous-signal detecting devices are worn on the subject, the propagation-signal producing and detecting devices are also worn on the subject. Thus, the pulse-wave-propagation-velocity measuring operation can be easily done.

However, it is possible to employ a propagation-signal producing device which is separate from the first heartbeat-synchronous-signal detecting device, and a propagation-signal detecting device which is separate from the second heartbeat-synchronous-signal detecting device. In this case, the apparatus can employ, as the first and second heartbeat-synchronous-signal detecting devices, conventional heartbeat-synchronous-signal detecting devices as they are.

According to a second aspect of the present invention, there is provided an apparatus for measuring a velocity at which a pulse wave propagates between a first portion and a second portion of a living subject, the apparatus comprising a bed on which the subject lies; a contour determining device which determines a contour of the subject lying on the bed; a blood-vessel-length determining means for determining a length of a blood vessel of the subject that is located between the first and second portions of the subject, based on the contour of the subject determined by the contour determining device and respective positions of the first and second portions of the subject in the contour; and a pulse-wave-propagation-velocity determining means for determining the velocity at which the pulse wave propagates between the first and second portions of the subject, based on the length of the blood vessel determined by the blood-vessel-length determining means.

According to this aspect, the contour determining device determines the contour of the subject whose pulse-wave propagation velocity is to be measured, and the blood-vessel-length determining means determines the length of the blood vessel based on the contour of the subject determined by the contour determining device and the respective positions of the first and second portions in the contour. Thus, the present apparatus can determine the length of the blood vessel with the same degree of accuracy as that with which a distance between the two portions on a body surface is measured. In addition, no skill is needed to determine blood-vessel length, and the time needed for the determination can be shortened.

According to a third aspect of the present invention, there is provided an apparatus for measuring a velocity at which a pulse wave propagates between a first portion and a second portion of a living subject, the apparatus comprising: a blood-vessel-image taking device which takes an image of a blood vessel of the subject; a blood-vessel-length determining means for determining a length of a portion of the blood vessel of the subject that is located between the first and second portions of the subject, based on the image of the blood vessel of the subject taken by the blood-vessel-image taking device; and a pulse-wave-propagation-velocity determining means for determining the velocity at which the pulse wave propagates between the first and second portions of the subject, based on the length of the portion of the blood vessel determined by the blood-vessel-length determining means.

According to this aspect, the blood-vessel-image taking device takes the image of the blood vessel and the blood-vessel-length determining means determines the length of the blood vessel based on the image of the blood vessel of the subject taken by the blood-vessel-image taking device. Thus, the present apparatus can determine the length of the blood vessel with a much higher accuracy than an accuracy with which a distance between the two portions on a body surface is actually measured.

BRIEF DESCRIPTION OF THE DRAWINGS

The above and optional objects, features, and advantages of the present invention will be better understood by reading the following detailed description of the preferred embodiments of the invention when considered in conjunction with the accompanying drawings, in which.

DETAILED DESCRIPTION OF PREFERRED EMBODIMENTS

Figure 1:
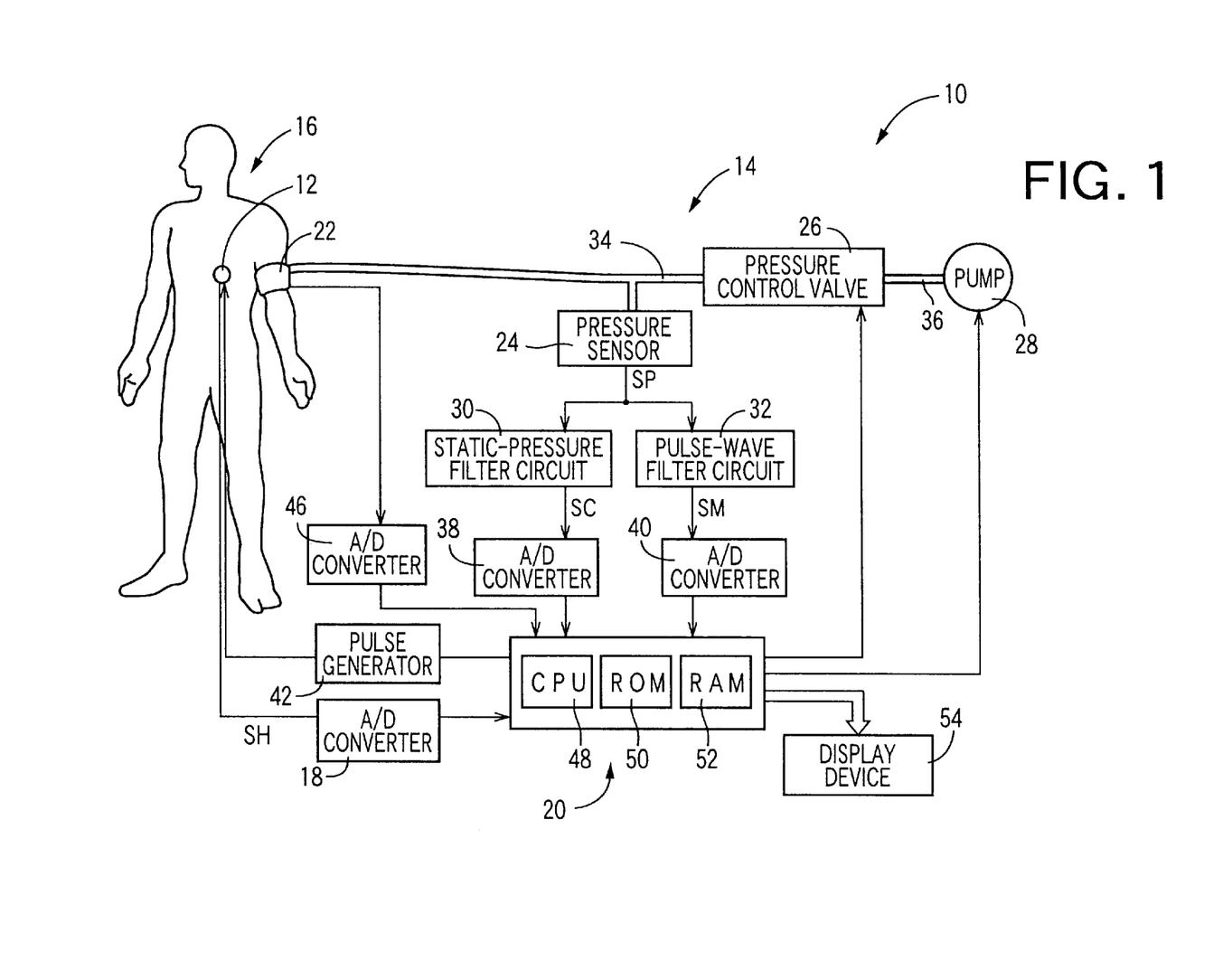
FIG. 1 is a diagrammatic view showing a construction of a pulse-wave propagation velocity measuring apparatus to which the present invention is applied.

Hereinafter, there will be described an embodiment of the present invention in detail by reference to the drawings. FIG. 1 is a diagrammatic view showing a construction of a pulse-wave propagation velocity measuring apparatus 10 to which the present invention is applied.

The pulse-wave propagation velocity measuring apparatus 10 includes a heart-sound microphone 12 functioning as a first heartbeat-synchronous-signal detecting device, and a brachial-pulse-wave detecting device 14 functioning as a second heartbeat-synchronous-signal detecting device. The heart-sound microphone 12 is worn on a prescribed portion of the chest of a patient 16 as a living subject, detects heart sounds produced from the heart of the patient, and supplies a heart-sound signal, SH, representing the detected heart sounds, to an electronic control device 20 via an A/D (analog-to-digital) converter 18. In the present embodiment, the prescribed portion of the chest of the patient corresponds to a first portion of the patient.

The brachial-pulse-wave detecting device 14 includes an inflatable cuff 22, a pressure sensor 24, a pressure control valve 26, an air pump 28, a static-pressure filter circuit 30, and a pulse-wave filter circuit 32. The cuff 22 includes a belt-like cloth bag and a rubber bag accommodated in the cloth bag, and is adapted to be wound around an upper arm of the patient 16. In the present embodiment, the upper arm corresponds to a second portion of the patient. The pressure sensor 24 and the pressure control valve 26 are connected via a piping 34 to the cuff 22, and the air pump 28 is connected via a piping 36 to the pressure control valve 26. The pressure control valve 26 adjusts a pressure of a pressurized air supplied from the air pump 28, and supplies the pressure-adjusted air to the cuff 22, or discharges the pressurized air from the cuff 22, so as to control an air pressure in the cuff 22.

The pressure sensor 24 detects the air pressure in the cuff 22, and supplies a pressure signal, SP, representing the detected air pressure, to a static-pressure filter circuit 30 and a pulse-wave filter circuit 32. The static-pressure filter circuit 30 includes a low-pass filter that extracts, from the pressure signal SP, a cuff-pressure signal, SC, representing a static component of the detected air pressure, i.e., a pressing pressure of the cuff 22 (hereinafter, referred to as the cuff pressure, PC). The filter circuit 30 supplies the cuff-pressure signal SC to the electronic control device 20 via an A/D converter 38. The pulse-wave filter circuit 32 includes a band-pass filter that extracts, from the pressure signal SP, a cuff-pulse-wave signal, SM, representing an oscillatory component of the detected air pressure that has prescribed frequencies. The filter circuit 32 supplies the cuff-pulse-wave signal SM to the control device 20 via an A/D converter 40. The oscillatory component represented by the cuff-pulse-wave signal SM is a brachial pulse wave that is transmitted to the cuff 22 from a brachial artery, not shown, of the upper arm being pressed by the cuff 22.

Figure 2:
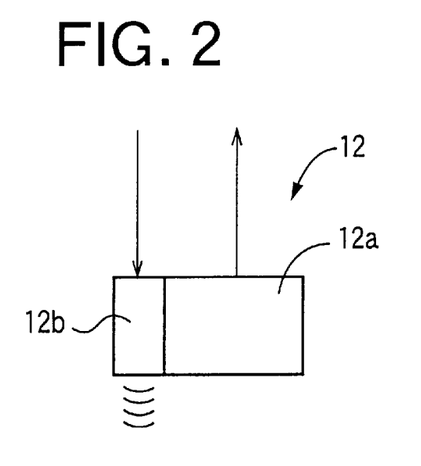
FIG. 2 is an illustrative view showing a structure of a heart-sound microphone employed in the apparatus of FIG. 1.

As shown in FIG. 2, the heart-sound microphone 12 includes a microphone portion 12a for detecting heart sounds, and a first oscillator 12b which is integral with the microphone portion 12a. The first oscillator 12b is an element that converts an electric signal into mechanical oscillation, and is connected to a pulse generator. When the control device 20 supplies a pulse-generation signal to the pulse generator 42, the generator 42 generates a pulse signal having a prescribed frequency equal to or higher than several hundred kilohertz, and the pulse signal is supplied to the first oscillator 12b. When the pulse signal is supplied to the first oscillator 12b, the first oscillator 12b is oscillated at the same frequency as that of the pulse signal, so that the first oscillator 12b produces a supersonic wave having the frequency. In the present embodiment, the supersonic wave produced by the first oscillator 12b corresponds to a propagation signal, and the first oscillator 12b functions as a propagation-signal producing device.

Figure 3:
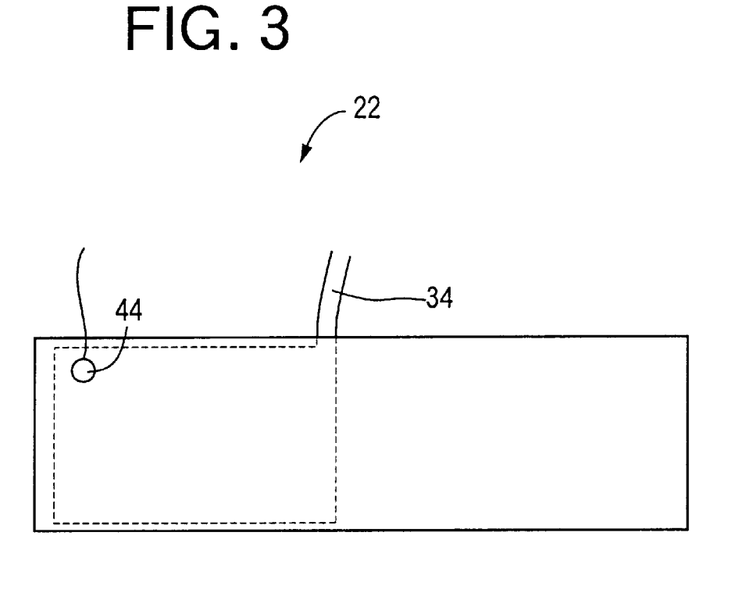
FIG. 3 is a view showing a cuff, employed in the apparatus of FIG. 1, in a state in which the cuff is developed.

FIG. 3 shows an inside surface of the cuff 22 being extended. A second oscillator 44 is fixed, to the inside surface of the cuff 22, at a position which assures that when the cuff 22 is worn on the upper arm, the second oscillator 44 is contacted with a body surface of the patient. The second oscillator 44 has a construction identical with that of the first oscillator 12b. However, the first oscillator 12b is used to convert the electric signal into the supersonic wave, whereas the second oscillator 44 is used to convert the supersonic wave into an electric signal. More specifically described, when the supersonic wave produced by the first oscillator 12b propagates through a body tissue of the patient 16 and reaches the second oscillator 44, the second oscillator 44 converts the supersonic wave into an electric signal, which is supplied via an A/D converter 46 to the electronic control device 20. Thus, the second oscillator 44 functions as a propagation-signal detecting device.

The electric control device 20 is provided by a so-called microcomputer including a CPU (central processing unit) 48, a ROM (read only memory) 50, a RAM (random access memory) 52, and an I/O (input-and-output) port, not shown. The CPU 48 processes signals according to the control programs pre-stored in the ROM 50 by utilizing the temporary-storage function of the RAM 52, and supplies drive signals via the I/O port to the air pump 28 and the pressure control valve 26 so as to control the cuff pressure PC. More specifically described, the CPU 48 controls the air pump 28 and the pressure control valve 26 to change and maintain the cuff pressure PC to and at a pre-set pulse-wave detecting pressure, e.g., 50 mmHg. This pulse-wave detecting pressure is pre-set at a pressure which is lower than a diastolic blood pressure of the upper arm of the patient and which assures that the cuff-pulse-wave signal SM extracted by the pulse-wave filter circuit 32 shows a sufficiently great magnitude. The ROM 50 stores, in advance, a velocity at which a supersonic wave propagates through a body tissue (hereinafter, this velocity will be referred to as the supersonic-wave propagation velocity). The supersonic-wave propagation velocity is, e.g., 1,530 m/sec.

The CPU 48 also functions as a blood-vessel-length determining means, and carries out a blood-vessel-length determining routine, described below. First, the CPU supplies the pulse-generation signal to the pulse generator 42, so that the first oscillator 12b provided in the heart-sound microphone 12 produces the supersonic wave having the prescribed frequency. Subsequently, the CPU judges whether the CPU has received, from the second oscillator 44, the electric signal having the same frequency as that of the supersonic wave. If a positive judgment is made, then the CPU determines, as a signal-propagation time, a time (sec) from the supplying of the pulse-generation signal (i.e., the production of the supersonic wave) to the reception of the electric signal. Then, the CPU divides the thus determined signal-propagation time by the supersonic-wave propagation velocity pre-stored in the ROM 50, and determines the thus obtained value as a blood-vessel length, L.

Moreover, the CPU 48 determines, as a pulse-wave propagation time, DT, a time difference between the time of occurrence of a prescribed point of the heart sounds (e.g., a start point of a second heart sound II) represented by the heart-sound signal SH supplied from the microphone 12 and the time of occurrence of a prescribed point of the brachial pulse wave (e.g., a dicrotic notch of the pulse wave) represented by the pulse-wave signal SM supplied from the pulse-wave filter circuit 32 in the state in which the cuff pressure PC is maintained at the pulse-wave detecting pressure. The pulse-wave propagation time DT is a time needed for the pulse wave to propagate from the aortic valve of the patient to the upper arm of the same. Finally, the CPU substitutes the thus determined pulse-wave propagation time DT and the blood-vessel length L for the following Expression 1 so as to determine a pulse-wave propagation velocity, PWV, at which the pulse wave propagates from the aorta to the upper arm and display the thus determined pulse-wave propagation velocity, PWV on a display device 54:

$$PWV = L/DT \qquad \text{(Expression 1)}$$

In the illustrated embodiment, the CPU 48 determines the length L of the blood vessel which is located between the two portions where the pulse-wave propagation velocity PWV is measured, and through which the supersonic wave is actually propagated. Thus, the blood-vessel length L can be determined with the same degree of accuracy as that with which the length L is actually measured on the body surface of the subject. In addition, since the blood-vessel length L can be determined by only wearing the first oscillator 12b on the chest and wearing the second oscillator 44 on the upper arm, the length L can be determined without a special skill and in a shortened time.

In addition, in the illustrated embodiment, the first oscillator 12b is integrally provided in the heart-sound microphone 12 and the second oscillator 44 is integrally provided in the cuff 22. Therefore, when the microphone 12 and the cuff 22 are worn on the patient 16, the first and second oscillators 12b, 44 are simultaneously worn on the patient 16. Thus, the pulse-wave propagation velocity PWV can be easily measured.

Next, there will be described a second embodiment of the present invention. The second embodiment relates to a pulse-wave propagation velocity measuring apparatus which differs from the pulse-wave propagation velocity measuring apparatus 10 as the first embodiment only with respect to devices and functions that are related to the determination of blood-vessel length L. Hereinafter, there will be described only the differences between the present apparatus as the second embodiment and the apparatus 10 as the first embodiment. The same reference numerals as used in the first embodiment are used to designate the corresponding parts of the present, second embodiment, and the description of those parts is omitted.

Figure 4:
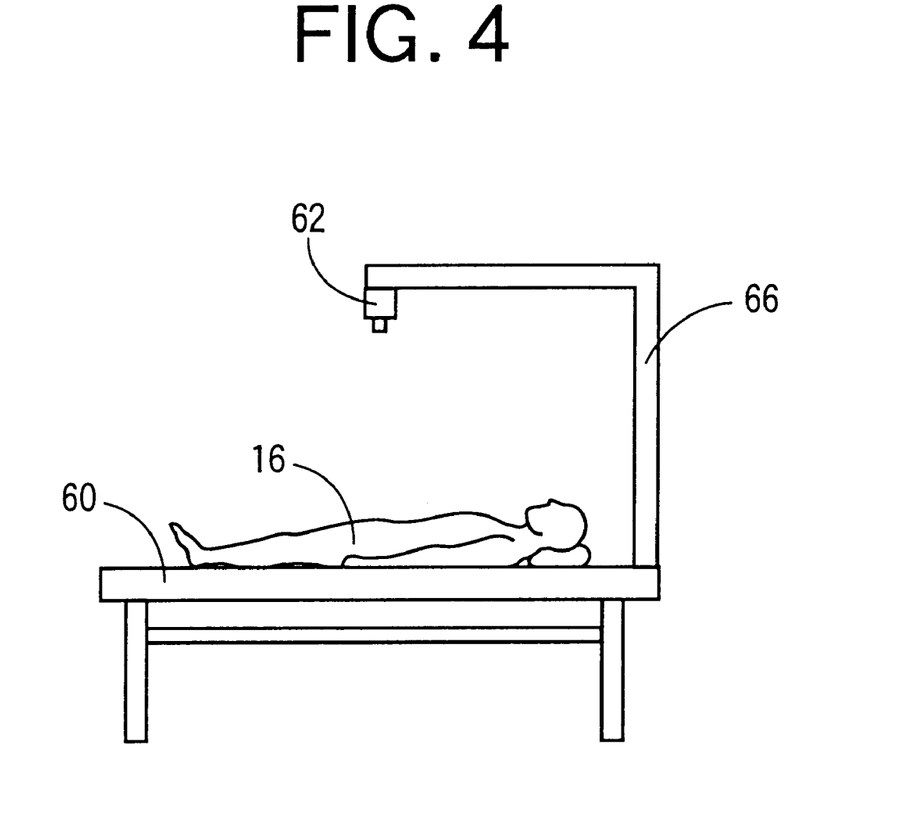
FIG. 4 is a view showing a bed and a patient camera which are employed in another pulse-wave propagation velocity measuring as a second embodiment of the present invention.

The pulse-wave propagation velocity measuring apparatus as the second embodiment does not employ the first oscillator 12b, the second oscillator 44, the pulse generator 42, or the A/D converters 18, 46 that are employed by the apparatus 10 to measure the blood-vessel length L, and employs a bed 60 and a patient camera 62 as shown in FIG. 4. In addition, the present pulse-wave propagation velocity measuring apparatus includes a control key, not shown, that is operable for operating the patient camera 62, and a keyboard, not shown, that is operable for processing an image taken by the patient camera 62.

The patient camera 62 is fixed to one end of a camera support 66 that is fixed to the bed 60, such that the camera 62 can take an image of the entirety of the bed 60. The patient camera 62 is, e.g., a CCD (charge-coupled device) camera that converts light into electric signals and supplies the electric signals to the electronic control device 20. The control device 20 processes an image represented by the electric signals supplied from the patient camera 62, thereby determining a two-dimensional contour of the patient 16. Thus, the patient camera 62 and the control device 20 cooperate with each other to function as a contour determining device.

Figure 5:
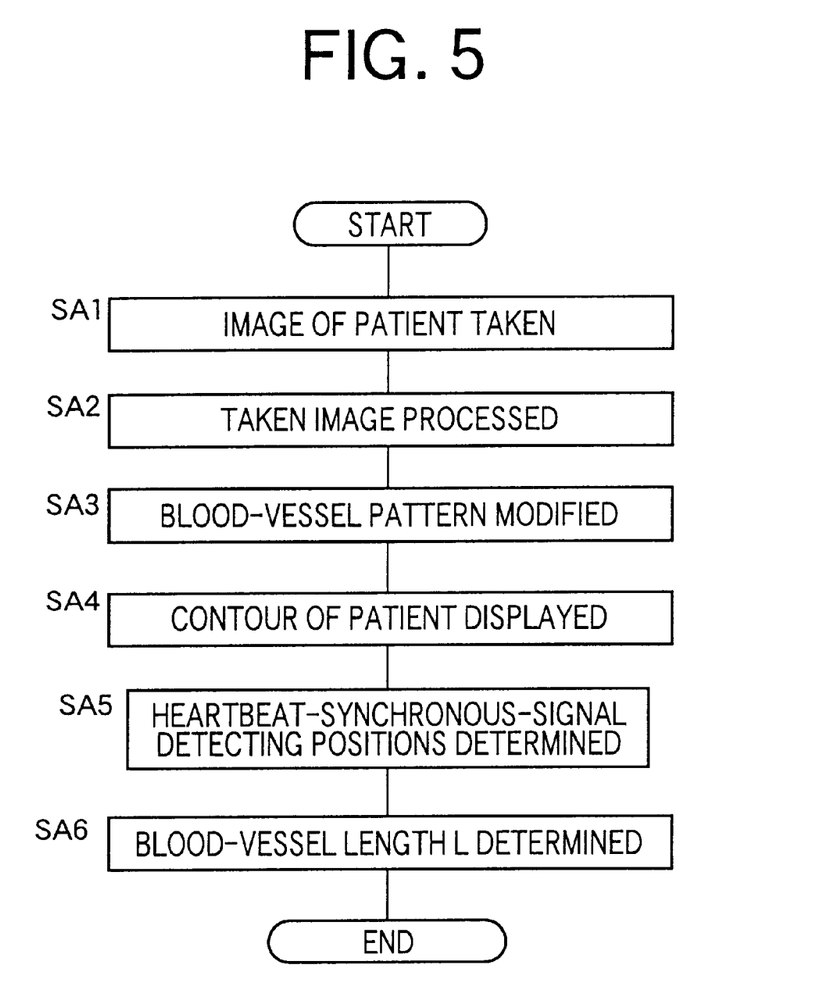
FIG. 5 is a flow chart for explaining a blood-vessel-length determining function of a CPU (central processing unit) employed in the apparatus of FIG. 4.

Also in the second embodiment, the CPU 48 of the control device 20 functions as a blood-vessel-length determining means. FIG. 5 shows a flow chart for explaining the blood-vessel-length determining function of the CPU of the pulse-wave propagation velocity measuring apparatus as the second embodiment. First, at Step SA1 (hereinafter, each term "Step(s)" is omitted), the above-describe control key is operated by a medical person such as a doctor or a nurse to take, with the patient camera 62, an image of the patient 16 who is taking a prescribed position on the bed 60.

Figure 6A:
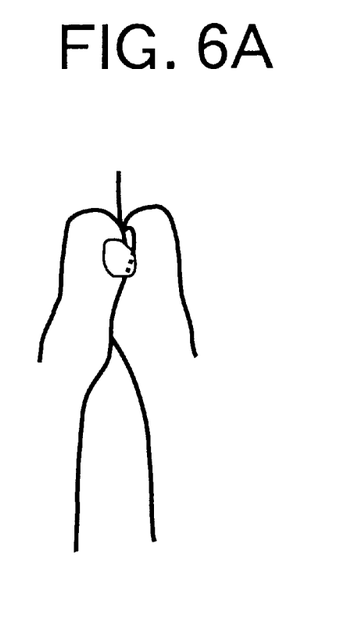
FIG. 6A is a view showing an example of a blood-vessel pattern pre-stored in a ROM (read only memory) of the apparatus of FIG. 4.
Figure 6B:
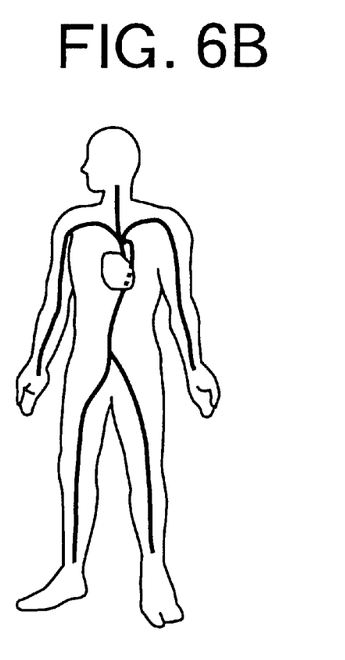
FIG. 6B is a view showing a contour of a patient displayed at Step SA4 of FIG. 5.

Then, at SA2, the CPU processes the image represented by the electric signals supplied from the patient camera 62 to the control device 20, thereby determining a contour (i.e., an outline) of the patient 16. Subsequently, at SA3, the CPU modifies a blood-vessel pattern pre-stored in the ROM 50, so that the modified blood-vessel pattern suits with the contour of the patient 16 determined at SA2. At SA4, the CPU operates the display device 54 to display the contour of the patient 16 and the modified blood-vessel pattern. FIG. 6A shows an example of the blood-vessel pattern pre-stored in the ROM 50; and FIG. 6B shows what is displayed by the display device 54 at SA4. At SA3, the CPU modifies, i.e., magnifies and/or reduces the blood-vessel pattern pre-stored in the ROM 50, in lengthwise and/or widthwise directions thereof, so that the modified blood-vessel pattern is positioned along respective centerlines of respective portions of the contour of the patient 16 determined at SA2.

After the contour of the patient 16 is displayed by the display device 54 at SA4, the CPU is allowed to receive two heartbeat-synchronous-signal detecting positions that are designated through operation of the above-described keyboard. When the keyboard is operated by the medical person to designate the position where the heart-sound microphone 12 is worn and the position where the cuff 22 is worn, the CPU determines, at SA5, the thus designated positions as the two heartbeat-synchronous-signal detecting positions. Then, at SA6, the CPU determines a provisional length of a blood vessel of the modified blood-vessel pattern that is located between the two heartbeat-synchronous-signal detecting positions determined at SA5, and determines a proper blood-vessel length L based on the thus determined provisional length and the magnification ratio and/or reduction ratio used at SA3.

After the blood-vessel length L is determined in this way, the heart-sound microphone 12 and the cuff 22 are worn on the patient 16, and a pulse-wave propagation velocity PWV is measured using the thus determined blood-vessel length L, in the same manner as described above with respect to the first embodiment.

As is apparent from the foregoing description of the second embodiment, the electronic control device 20 processes the image of the patient 16 taken by the patient camera 62, thereby determining the contour of the patient, and the CPU 48 determines the blood-vessel length L based on the respective positions where the heart-sound microphone 12 and the cuff 22 are worn in the thus determined contour of the patient. Thus, the blood-vessel length L can be determined with the same degree of accuracy as that with which an actual length between the positions where the microphone 12 and the cuff 22 are worn is measured on the body surface of the patient. In addition, the blood-vessel length L can be determined without a special skill and in a shortened time.

Next, there will be described a third embodiment of the present invention. The third embodiment relates to a pulse-wave propagation velocity measuring apparatus which differs from the pulse-wave propagation velocity measuring apparatus 10 as the first embodiment, or the pulse-wave propagation velocity measuring apparatus as the second embodiment, only with respect to devices and functions that are related to the determination of blood-vessel length L. Hereinafter, there will be described only the differences between the present apparatus as the second embodiment and the apparatus 10 as the first embodiment. Hereinafter, only differences between the third embodiment and the first or second embodiment will be described.

The pulse-wave propagation velocity measuring apparatus as the third embodiment does not employ the bed 60 or the patient camera 62 that are employed by the apparatus as the second embodiment, and employs an X-ray CT (computerized tomography) scan device, not shown, known in the art.

Figure 7:
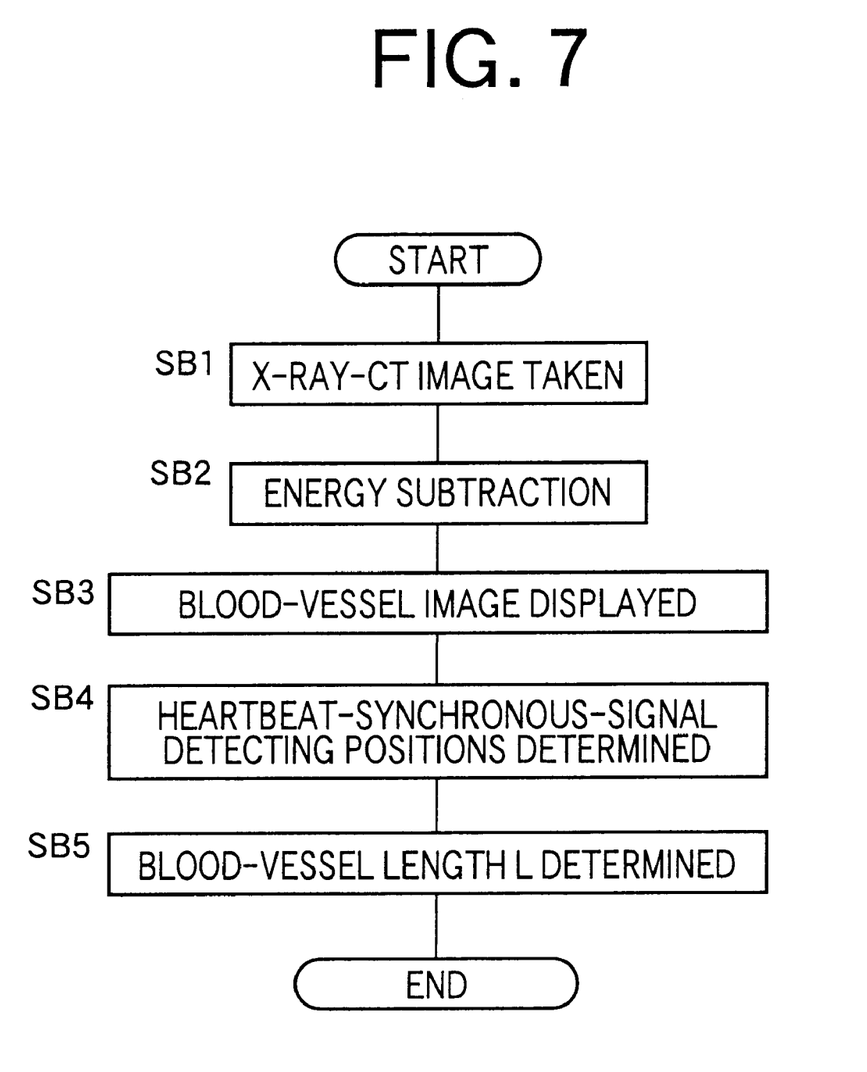
FIG. 7 is a flow chart for explaining a blood-vessel-length determining function of a CPU employed in another pulse-wave propagation velocity measuring as a third embodiment of the present invention.

Also in the third embodiment, the CPU 48 of the control device 20 functions as a blood-vessel-length determining means. FIG. 7 shows a flow chart for explaining the blood-vessel-length determining function of the CPU 48 of the pulse-wave propagation velocity measuring apparatus as the third embodiment.

First, at Step SB1 (hereinafter, each term "Step(s)" is omitted), the X-ray CT scan device, not shown, is operated to use two X-rays having different energy levels for taking respective X-ray images of a whole body of a patient 16.

Then, at SB2, the CPU subjects the thus taken two images to a well-known energy subtraction method. More specifically described, the CPU subtracts one of the two images from the other image, and obtains an image of a blood vessel of the patient based on the difference of respective reactions of the body of the patient to the two X-rays having the different energy levels. Thus, in the present embodiment, the X-ray CT scan device and the electronic control device 20 cooperate with each other to function as a blood-vessel-image taking device.

Then, at SB3, the display device 54 displays the blood-vessel image taken at SB2. Subsequently, at SB4, the CPU determines two heartbeat-synchronous-signal detecting positions in the same manner as that employed at SA5 of FIG. 5. Then, at SB5, the CPU determines, as a length L of a blood vessel of the patient, a distance between the two heartbeat-synchronous-signal detecting positions determined at SB4 that is measured in the blood-vessel image obtained at SB2.

As is apparent from the foregoing description of the third embodiment, the electronic control device 20 processes the X-ray image taken by the X-ray CT scan device, so as to determine the image of the blood vessel of the patient 16, and the CPU 48 determines the blood-vessel length L based on the blood-vessel image. Thus, the blood-vessel length L can be determined with a much higher degree of accuracy than that with which a distance between two portions is actually measured on a body surface.

While the present invention has been described in detail in its preferred embodiments by reference to the drawings, it is to be understood that the present invention may otherwise be embodied.

For example, in the second embodiment, the patient camera 62 is sensitive to light and converts the light into electric signal. However, the patient camera 62 may be a different sort of camera, for example, a thermograph camera that detects thermal energy emitted from an object.

In the second embodiment, the patient camera 62 and the electronic control device 20 cooperate with each other to function as the contour determining device. However, the patient camera 62 may be replaced with a sheet which entirely covers the bed 60 and includes a number of pressure-sensing elements distributed all over the sheet. This sheet can be used to determine a contour of a patient 16. In this case, the control device determines, as the contour of the patient 16, an outer edge of an area where the pressure sensing elements senses the pressure of the patient. The pressure sensing elements may be replaced with bio-magnetism sensing elements.

In the second embodiment, the patient camera 62 is a fixed one which can take, at once, a two-dimensional image of the entire body of the patient 16. However, the patient camera 62 may be replaced with a camera which can take a two-dimensional or one-dimensional image and can be moved in a direction parallel to, or perpendicular to, the bed 60 so as to scan an entire body of a patient 16.

In the third embodiment, the X-ray CT scan device may be replaced with an MRI (magnetic resonance imaging) device, or an ultrasonic echo device, so as to take an image of a blood vessel.

In each of the illustrated embodiments, the chest of the patient 16 is used as the first portion and the upper arm of the patient is used as the second portion. However, other portions of the patient may be used as the first or second portion. For example, a neck portion, a wrist, a femoral portion, an ankle, etc. may be used as the first or second portion.

The present invention may be embodied with other various changes without departing from the spirit of the invention.

What is claimed is:

1. An apparatus for measuring a velocity at which a pulse wave propagates between a first portion and a second portion of a living subject, the apparatus comprising:

a propagation-signal producing device which is adapted to be worn on the first portion of the subject and produces a propagation signal;

a propagation-signal detecting device which is adapted to be worn on the second portion of the subject and detects the propagation signal that has been produced by the propagation-signal producing device, has propagated through a body tissue of the subject, and has reached the second portion;

a blood-vessel-length determining means for determining a length of a blood vessel of the subject that is located between the first and second portions of the subject, based on a signal propagation time from a time when the propagation signal is produced by the propagation-signal producing device, to a time when the propagation signal is detected by the propagation-signal detecting device, and a pre-stored velocity at which the propagation signal propagates through a body tissue of a human person; and a pulse-wave-propagation-velocity determining means for determining the velocity at which the pulse wave propagates between the first and second portions of the subject, based on the length of the blood vessel determined by the blood-vessel-length determining means.

2. An apparatus according to claim 1, further comprising a memory device which stores the velocity at which the propagation signal propagates through the body tissue of the human person.

3. An apparatus according to claim 1, further comprising:

a first heartbeat-synchronous-signal detecting device which is adapted to be worn on the first portion of the subject and detects a first heartbeat-synchronous signal from the first portion; and a second heartbeat-synchronous-signal detecting device which is adapted to be worn on the second portion of the subject and detects a second heartbeat-synchronous signal from the second portion, wherein the pulse-wave-propagation-velocity determining means determines the velocity at which the pulse wave propagates between the first and second portions of the subject, by dividing the length of the blood vessel determined by the blood-vessel-length determining means, by a pulse-wave propagation time from a time when the first heartbeat-synchronous signal is detected by the first heartbeat-synchronous-signal detecting device, to a time when the second heartbeat-synchronous signal is detected by the second heartbeat-synchronous-signal detecting device.

4. An apparatus according to claim 3, wherein the propagation-signal producing device is supported by the first heartbeat-synchronous-signal detecting device, and the propagation-signal detecting device is supported by the second heartbeat-synchronous-signal detecting device.

5. An apparatus according to claim 1, further comprising a display device which displays the velocity determined by the pulse-wave-propagation-velocity determining means.

* * * * *